(12) United States Patent
Mercola et al.

(10) Patent No.: US 7,910,305 B2
(45) Date of Patent: Mar. 22, 2011

(54) METHODS FOR SCREENING FOR COMPOUNDS THAT MODULATE INSULIN PROMOTER ACTIVITY

(75) Inventors: Mark Mercola, La Jolla, CA (US); Fred Levin, La Jolla, CA (US); Pamela Itkin-Ansari, La Jolla, CA (US)

(73) Assignee: The Burnham Institute for Medical Research, La Jolla, CA (US)

( * ) Notice: Subject to any disclaimer, the term of this patent is extended or adjusted under 35 U.S.C. 154(b) by 75 days.

(21) Appl. No.: 11/992,028

(22) PCT Filed: Sep. 14, 2006

(86) PCT No.: PCT/US2006/036133
§ 371 (c)(1),
(2), (4) Date: Mar. 14, 2008

(87) PCT Pub. No.: WO2007/035546
PCT Pub. Date: Mar. 29, 2007

(65) Prior Publication Data
US 2009/0264309 A1 Oct. 22, 2009

Related U.S. Application Data

(60) Provisional application No. 60/717,647, filed on Sep. 15, 2005.

(51) Int. Cl.
*C12Q 1/68* (2006.01)
(52) U.S. Cl. .......... 435/6; 435/354; 435/366; 435/320.1
(58) Field of Classification Search ........................ None
See application file for complete search history.

(56) References Cited

U.S. PATENT DOCUMENTS

| | | | |
|---|---|---|---|
| 2002/0071824 A1* | 6/2002 | Giannoukakis et al. | 424/85.1 |
| 2003/0129170 A1 | 7/2003 | Iacovitti | |
| 2003/0215804 A1* | 11/2003 | Berggren et al. | 435/6 |
| 2004/0152168 A1 | 8/2004 | German | |
| 2005/0003547 A1 | 1/2005 | Spencer | |

OTHER PUBLICATIONS

Castaing, M. et al., "Efficient restricted gene expression in beta cells by lentivirus-mediated gene transfer into pancreatic stem/progenitor cells," Diabetologia (2005) 48:709-719.
Follenzi, A. et al., "Gene transfer by lentiviral vectors is limited by nuclear translocation and rescued by HIV-1 pol sequences," Nature Genetics (2000) 25:217-222.
Leibiger, B. et al., "Short-term regulation of insulin gene transcription by glucose," Proc. Natl. Acad. Sci. USA, vol. 95, pp. 9307-9312, Aug. 1998.
Itkin-Ansari, P. et al., "E47 as a Regulator of Beta-Cell Growth and Differentiation," Diabetes, vol. 54, No. Suppl. 1, Jun. 2005.
Itkin-Ansari, P. et al., "NeuroD1 in the Endocrine Pancreas: Localization and Dual Function as an Activator and Repressor," Developmental Dynamics 233:946-953, 2005.

* cited by examiner

*Primary Examiner* — James S Ketter
(74) *Attorney, Agent, or Firm* — Sam K. Tahmassebi; TechLaw LLP

(57) ABSTRACT

Compositions and methods are provided for screening for compounds that modulate insulin promoter activity. Vectors that express green fluorescent protein under the control of the human insulin promoter are introduced into mouse and human cells in which the insulin promoter is expressed in a glucose-responsive manner. Such cells are then used to screen for compounds that modulate insulin promoter activity.

41 Claims, 7 Drawing Sheets

METHODS FOR SCREENING FOR COMPOUNDS THAT MODULATE INSULIN PROMOTER ACTIVITY

CROSS-REFERENCE TO RELATED CASES

This application claims priority from U.S. provisional patent application Ser. No. 60/717,647, filed Sep. 15, 2005, which is incorporated herein by reference.

STATEMENT OF GOVERNMENT RIGHTS

The invention was supported, at least in part, by a grant from the Government of the United States of America (grant no. R01 DK68754 from the National Institutes of Health). The Government may have certain rights to the invention.

FIELD OF THE INVENTION

The present inventions relates to the field of drug screening, in particular, screening for substances that modulate insulin production.

BACKGROUND

The cardinal property of pancreatic beta cells, shared by no other cell in the body, is high level expression of the insulin gene. The cis and trans elements that affect insulin promoter activity have been studied for many years but it is clear that our understanding is limited. In particular, while the promoter elements that determine beta-cell specificity of insulin expression are well understood, the pathways that signal to the insulin promoter have not been investigated extensively, in part because of a lack of in vitro models. There is a need for effective screening methods in order to identify substances, e.g., chemical compounds, that modulate insulin production, that is, increase or decrease insulin production.

SUMMARY OF THE INVENTION

The present invention provides compositions and methods for screening for compounds that modulate insulin expression in mammalian cells.

According to one embodiment of the invention, vectors are provided that comprise a human insulin gene promoter polynucleotide sequence operably linked to a polynucleotide that encodes a marker polypeptide, such as a green fluorescent protein polynucleotide sequence, wherein destabilized enhanced green fluorescent protein is expressed upon introduction of the vector into a cell selected from the group consisting of a MIN6 mouse insulinoma cell and a human T6PN/E47MER cell. Such vectors may, for example, be viral vectors, including, but not limited to lentiviral vectors such as pRRL.SIN-18.cPPT.hINS-EGFP.WPRE, in which an destabilized enhanced green fluorescent protein is expressed under the control of a human insulin promoter, as described in detail in Example 1.

Also provided are cells comprising such vectors (i.e., cells into which such vectors are introduced by infection or other standard means). Such cells include pancreatic beta cells. Representative cells comprising the vectors of the present invention include but are not limited to murine cells, such as MIN6 mouse insulinoma cells, and human cells, such as T6PN/E47$^{MER}$ cells.

Also provided are methods of identifying a compound that modulates insulin gene expression. Such method comprising: (a) providing a cell comprising a vector that comprises a human insulin gene promoter polynucleotide that is operably linked to a marker polypeptide, such as, for example, an enhanced green fluorescent protein polynucleotide, wherein the marker polypeptide is expressed at a baseline level in the cell; (b) contacting the cell with a candidate compound; and (c) detecting a modulation in expression of the marker polypeptide in the cell compared to the baseline level as a result of contacting the cell with the candidate compound. Such screening methods may further comprise, for example, determining whether modulation of expression of enhanced green fluorescent protein by the candidate compound is dose-responsive; determining whether the candidate compound modulates expression of insulin by a mammalian insulin-producing cell; and/or determining whether the candidate compound modulates expression of insulin by a mammalian insulin-producing cell by RT-PCR. Vectors and cells used in such methods are similar to those describe above.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below.

DETAILED DESCRIPTION OF THE INVENTION

Definitions and Methods

Figure 1:
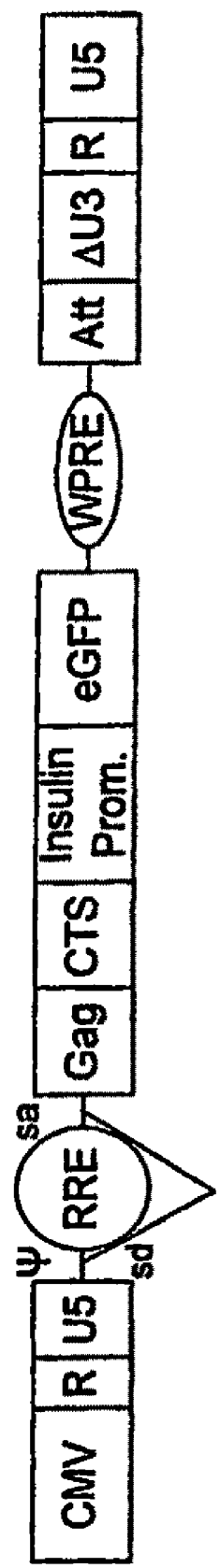
FIG. 1 shows the structure of a lentiviral vector expressing destabilized enhanced green fluorescent protein (eGFP) from the human insulin promoter. This vector pRRL.SIN-18.cPPT.hINS-EGFP.WPRE, expresses a destabilized enhanced green fluorescent protein (EGFP) reporter gene driven by the human insulin gene (hIns) promoter.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994.

"Polynucleotide." The term "polynucleotide" refers to a polymer of nucleotide monomers, including but not limited to ribonucleotides or deoxyribonucleotides or nucleotide analogues. Polynucleotides include, for example, DNA and RNA molecules, including cDNA, genomic DNA, primers, probes, vectors, and so on, and include single- and double-stranded forms thereof. Polynucleotides according to the invention may be chemically modified by well known methods by labeling, coupling to solid supports, etc.

"Cell". As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

"Mammal". As used herein, the term "mammal" includes any mammalian species, including, but not limited to, murine (e.g., mouse or rat), human, monkey, dog, cat, horse, etc.

"Isolated". By "isolated" polynucleotide(s) is intended a polynucleotide (i.e., a nucleic acid molecule, e.g., DNA or RNA), which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

"Operably Linked". Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Recombinant". A "recombinant" nucleic acid is made by an artificial combination of two otherwise separated segments of sequence, e.g., by chemical synthesis or by the manipulation of isolated segments of nucleic acids by genetic engineering techniques.

"Modulate". As used herein, the term "modulate" means to detectably change the expression of an expressible polynucleotide sequence in any detectable fashion, including but not limited to increasing or decreasing the level of expression, the timing of expression, the cell, tissue, organ or other specificity of expression, or any other aspect of gene expression. A modulation of gene expression may be detected by any know means, including, but not limited to, detecting a change in the level of mRNA transcription, of protein encoded by the polynucleotide, of enzymatic activity corresponding to an encoded protein, etc.

Preparation of Recombinant or Polynucleotides: Vectors, Transformation, Host cells. Natural or synthetic nucleic acids according to the present invention can be incorporated into recombinant polynucleotide constructs, typically DNA constructs, capable of introduction into and replication in a host cell. For example, such a construct may be a vector that includes a replication system and sequences that are capable of transcription and translation of a polypeptide-encoding sequence in a given host cell.

For the practice of the present invention, conventional compositions and methods for preparing and using vectors and host cells are employed.

A cell, tissue, organ, or organism into which has been introduced a foreign polynucleotide, such as a recombinant vector, is considered "transformed", "transfected", or "transgenic." A "transgenic" or "transformed" cell or organism also includes progeny of the cell or organism.

A number of vectors suitable for use with mammalian or other eukaryotic and prokaryotic cells, including but not limited to murine and human cells, are well known to the skilled practitioner. Typically, mammalian expression vectors include, for example, one or more polypeptide-encoding polynucleotide sequences under the transcriptional control of 5' and 3' regulatory sequences and a dominant selectable marker. Such mammalian expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal. The vector may be, for example, a phage, plasmid, viral or retroviral vector, depending on the use, and may be replication competent or replication defective. If a viral vector is replication defective, viral propagation generally will occur only in complementing host cells.

Recombinant constructs may be introduced into host cells using well known techniques such as infection, transduction, transfection, transvection, electroporation and transformation. Expression vectors include chromosomal-, episomal- and virus-derived vectors, e.g., vectors derived from bacterial plasmids, bacteriophage, yeast episomes, yeast chromosomal elements, viruses such as lentiviruses, baculoviruses, papova viruses, vaccinia viruses, adenoviruses, fowl pox viruses, pseudorabies viruses and retroviruses, and vectors derived from combinations thereof, such as cosmids and phagemids. A polypeptide-encoding polynucleotide insert is operatively linked to an appropriate promoter. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

Expression vectors may include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include bacterial cells, such as *Escherichia coli, Streptomyces* and *Salmonella typhimurium* cells; fungal cells, such as yeast cells; insect cells such as Drosophila S2 and Spodoptera Sf9 cells; animal cells such as mouse insulinoma (MIN6), human T6PN/E47MER, CHO, COS and Bowes melanoma cells; and plant cells. Appropriate culture media and conditions for the above-described host cells are known in the art.

Vectors useful for the practice are invention are described in the Examples. In addition, vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Eukaryotic vectors include, but are not limited to, pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

The Examples describe the use of the human insulin promoter in the practice of the present invention. In addition, bacterial promoters suitable for use for various purposes include the *E. coli* lacI and lacZ promoters, the T3 and T7 promoters, the gpt promoter, the lambda PR and PL promoters and the trp promoter. Eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Transcription by higher eukaryotes may be increased by inserting an enhancer sequence into the vector. Enhancers are cis-acting elements of DNA, usually about from 10 to 300 basepairs that act to increase transcriptional activity of a promoter in a given host cell-type. Examples of enhancers include but are not limited to the SV40 enhancer, which is located on the late side of the replication origin atbp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

Having generally described the invention, the same will be more readily understood by reference to the following examples, which are provided by way of illustration and are not intended as limiting. It is therefore to be understood that within the scope of the appended claims, the invention may be practiced otherwise than as specifically described herein.

EXAMPLE 1

Preliminary Screening of Compounds from the ChemBridge DiverSet Library Yielded Candidate Compounds that Regulate the Insulin Promoter Both Positively and Negatively, with a z' Value of 0.74 Calculated for the Increase in Insulin Promoter Activity and a z' Value of 0.43 for Inhibition of Insulin Promoter Activity The cardinal property of pancreatic beta-cells, shared by no other cell in the body, is high level expression of the insulin gene. The cis and trans elements that affect insulin promoter activity have been studied for many years, but it is clear that our understanding is limited. In particular, while the promoter elements that determine beta-cell specificity of insulin expression are well understood, the pathways that signal to the insulin promoter have not been investigated extensively, in part because of a lack of in vitro models.

We have developed a screen for small molecule compounds that modulate insulin promoter activity. Identifying these compounds and eventually their targets should provide insights into the signaling pathways that control insulin expression. The assay is based upon a mouse insulinoma, MIN6, that normally expresses insulin mRNA. This cell was engineered to stably contain two cassettes that use a fluorescent reporter protein to monitor insulin promoter activity and a housekeeping gene activity. The primary assay is to detect compounds that alter expression of an insulin promoter-destabilized eGFP reporter cassette in mouse insulinoma (MIN6) cells relative to that of a housekeeping gene, heat shock protein 68, the promoter of which is used in a second cassette to direct expression of destabilized dsRED2. A secondary assay may be used to confirm the hits and would further verify modulation of endogenous insulin mRNA expression relative to control mRNAs by RT-PCR. Like all cultured insulin-producing cells, MIN6 cells produce substantially less insulin mRNA and protein than do normal beta-cells in the intact pancreas. Thus, this allows the identification of compounds that both stimulate as well as suppress insulin production. The small molecule modulators of insulin mRNA synthesis are useful tools to probe the regulatory pathways that control insulin secretion. Knowledge of the pathways and means to modulate them are expected to lead to a knowledge base that will be applied to the treatment of type I and II diabetes. Preliminary studies indicate that the Insulin promoter-eGFP reporter transgene mimics the activity of the endogenous insulin gene. Assay parameters have been optimized, consolidated into a standard operating procedure and used to perform a pilot screen of 8,000 compound subset of the ChemBridge DiverSet collection. Hits that increased and decreased insulin gene expression were identified and confirmed. These hits were used to calculate a z' value of 0.74 for increase and 0.43 for decrease in eGFP.

Materials and Methods

Beta-Cell Models Suitable for Screens. Pancreatic beta-cells are the only cell type that expresses the insulin gene. Therefore, any screen directed at insulin promoter activity is desirably done using a beta-cell or beta-cell model. Primary beta-cells are in short supply and are difficult to work with, having a strong tendency to undergo apoptosis when manipulated, making them difficult to maintain in monolayer culture. Therefore, screens must utilize beta-cell models. Rodent insulinoma cell lines have been studied for many years. The MIN series of cell lines was developed from transgenic mice expressing the SV40 T antigen gene from an 1867 bp human insulin promoter fragment (Miyazaki et al., Endocrinology 127:126-132, 1990). MIN6, particularly in early passages, exhibits glucose-responsive insulin secretion at physiologic glucose concentrations. While later passages tend to lose this property, Min6 cells stably retain substantial levels of insulin gene expression indefinitely.

Although insulinoma cells such as MIN6 express large amounts of insulin mRNA and protein, the levels are still less than in a healthy beta cell in an intact pancreas. Thus, this screen is designed to detect small molecule probes that will increase as well as decrease expression.

This assay has unique aspects relative to screening for compounds that affect insulin promoter activity in a human pancreatic endocrine progenitor line. The human endocrine cell line is at a relatively more immature state. Moreover, human and rodent beta-cells differ in many characteristics, including the number of insulin genes and some features of how the insulin gene is regulated (Ohneda et al., Semin. Cell Dev. Biol. 11:227-233, 2000). Comparing results from the two insulin promoter screens to one another, one with human and one with murine cells, assists in mechanistic studies to determine the targets of the identified compounds and also to prioritize the compounds that will be studied in greater detail and brought forward into structure-activity and lead optimization studies that involve substantial chemistry resources.

Engineering of MIN6 for Image-Based, High Throughput Screening. A lentiviral vector pRRL.SIN-18.cPPT.hINS-eG-FPdestabilized.WPRE (shown in FIG. 1) was engineered to express a destabilized version of the enhanced green fluorescent protein (eGFP) reporter gene (Li et al., J. Biol. Chem. 273:34970-34975, 1998) driven by the human insulin gene (hINS) promoter as follows: the 1.4-kb SalI-HindIII hIns promoter sequence from plasmid pFOXCAT-1.4hIns1 1, kindly provided to us by M. German, was subcloned into SalI-HindIII sites in pBluescript SK−, excised with SalI-BamHI and ligated into XhoI-BamHI in pRRL.SIN-18.cPPT.hPGK-EGFP.WPRE 2 to substitute for hPGK promoter sequence. Vector supernatants were prepared by transient calcium phosphate-mediated co-transfection of 293T cells as previously described (Soneoka et al., Nucl. Acids Res. 23:628-633, 1995). 293T cells, at $2\times10^7$ cells per 15-cm plate in DMEM10 medium (Dulbecco's modified Eagle's medium containing 10% (v/v) fetal bovine serum (FBS), penicillin (100 U/ml), streptomycin (100 ug/ml), and 2 mM L-glutamine) were transfected with 35 micrograms of transfer vector plasmid: 25 ug of pCMV ΔR8.91 packaging plasmid 4, and 10.5 ug of pMD.G(VSV-G) envelope plasmid. 12-15 hours after transfection the medium was replaced with serum-free UltraCULTURE medium (Cambrex, East Rutherford, N.J., USA). Viral supernatants harvested at 24 to 72 hours were 0.45 μm filtered and concentrated 100- to 200-fold by ultrafiltration using Centricon Plus-80 units (Millipore, Bedford, Mass., USA), yielding titers of approximately $10^9$ transducing units (TU) per milliliter 5, determined by transduction of 293T cells with serial dilutions of the pRRL.SIN-18.cPPT.hPGK-EGFP.WPRE viral supernatant and FACS analysis to determine the percentage of EGFP-expressing cells. A similar vector was constructed to express a destabilized version of dsRED2 (Clonetech) under control of the ubiquitously expressed hsp68 promoter. Both of these proteins have reported half-lives on the order of 2-4 hours. Vector supernatants were prepared by transient calcium phosphate-mediated co-transfection of 293T cells as previously described (Soneoka et al., Nucl. Acids Res. 23:628-633, 1995). 293T cells, at $2\times10^7$ cells per 15-cm plate in DMEM10 medium (Dulbecco's modified Eagle's medium containing 10% (v/v) fetal bovine serum (FBS), penicillin (100 U/ml), streptomycin (100 μg/ml), and 2 mM L-glutamine) were transfected with 35 micrograms of transfer vector plasmid: 25 μg of pCMV ΔR8.91 packaging plasmid 4, and 10.5 μg of pMD.G(VSV-G) envelope plasmid. 12-15 hours after transfection the medium was replaced with serum-free UltraCULTURE medium (Cambrex, East Rutherford, N.J., USA). Viral supernatants harvested at 24 to 72 hours were 0.45 μm filtered and concentrated 100- to 200-fold by ultrafiltration using Centricon Plus-80 units (Millipore, Bedford, Mass., USA), yielding titers of approximately $10^9$ transducing units (TU) per milliliter5, determined by infection of 293T cells with serial dilutions of the viral supernatants containing a ubiquitous promoter (e.g., hsp68) and fluorescence-activated cell sorting (FACS) analysis to determine the percentage of fluorescent protein-expressing cells.

To demonstrate specificity of the hINS promoter, hINS-eGFP virus was used to infect the mouse insulinoma cell line Min6 and the cervical carcinoma cell line HeLa. High level GFP expression was observed in MIN6 but none in HeLa, consistent with the endogenous insulin promoter activity in those cell lines. Similar results were obtained with primary beta cells and fibroblasts.

Stable MIN6 lines were generated using the lentiviruses to introduce hINS-destabilized eGFP and hsp68-destabilized dsRED2 gene cassettes. Stable cell lines were subcloned. Clones with intermediate levels of dsRED2 and eGFP fluorescence were retained for further study. A pilot screen was performed with one clone, but the bioactivity of hits from the pilot screen was confirmed (see below) on a second clone as a demonstration of fidelity.

Figure 2:
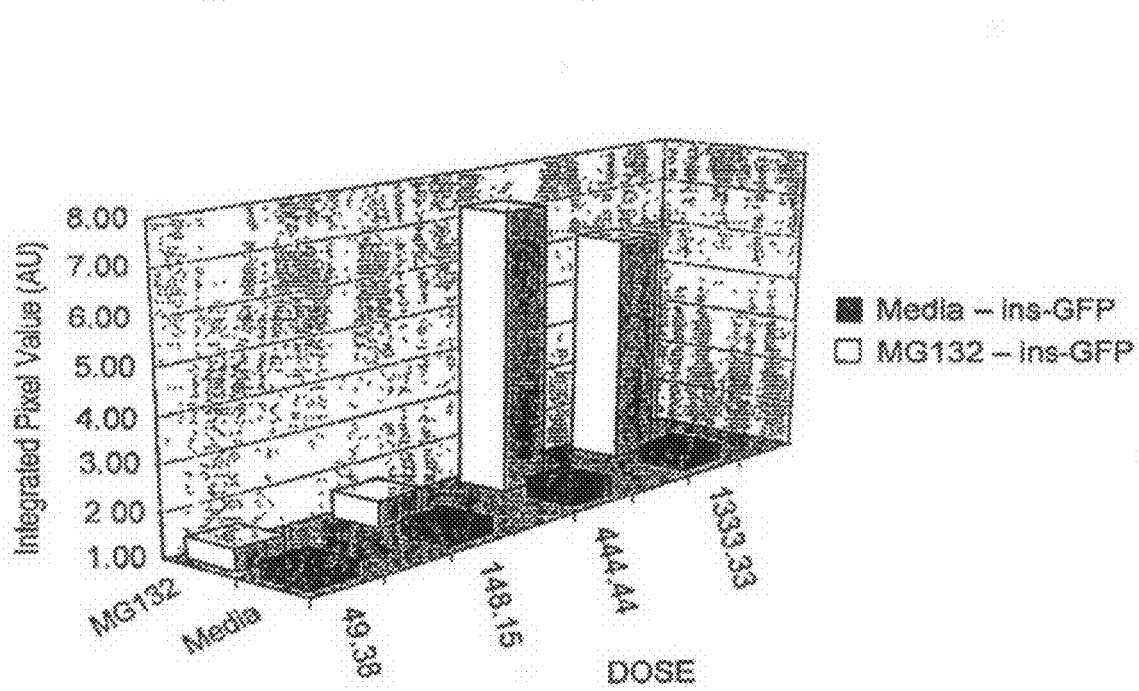
FIG. 2 shows the dose responsiveness of eGFP fluorescence in engineered MIN6 cells. Compounds were added over a three-fold titration series (concentrations in nM). (A) Exposure to the proteasome inhibitor MG132 stimulates a dose-dependent increase in eGFP fluorescence as would be expected by blocking degradation of the destabilized fluorescent protein. (B) Conversely, the protein synthesis inhibitor cyclohexamide caused a decrease in fluorescence intensity, reflecting a block to new protein synthesis. Data are an average of replicate wells from an assay performed in 384-well plates and imaged 48 hours following compound addition.
Figure 2:
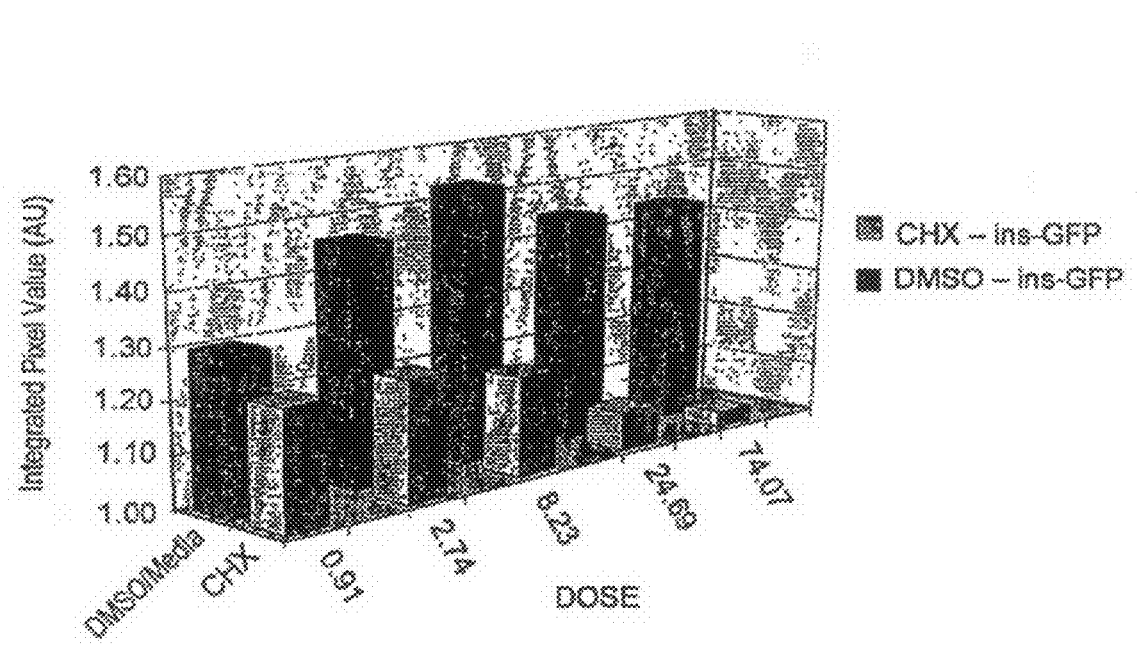

FIG. 2 shows the fluorescence of the eGFP in control and in response to positive and negative control compounds was determined. A test assay was done in replicates of eight wells each in 384-well plates. For the positive control, cells were exposed to MG132, which blocks proteosome function and should stabilize the fluorescent proteins and thereby increase fluorescence, and cyclohexamide, which blocks protein synthesis and should decrease fluorescence. We observed a dose-dependent increase and decrease in fluorescence, respectively, when the cells were evaluated at 48 hrs after compound addition. We conclude that the decrease in the intensity of the fluorescent proteins in this assay is consistent with expectations based on published data and is suitable to reveal a change in insulin or hsp68 expression after the 48 hr timeframe planned for this assay. We next developed an assay protocol to automate the screen.

Figure 3:
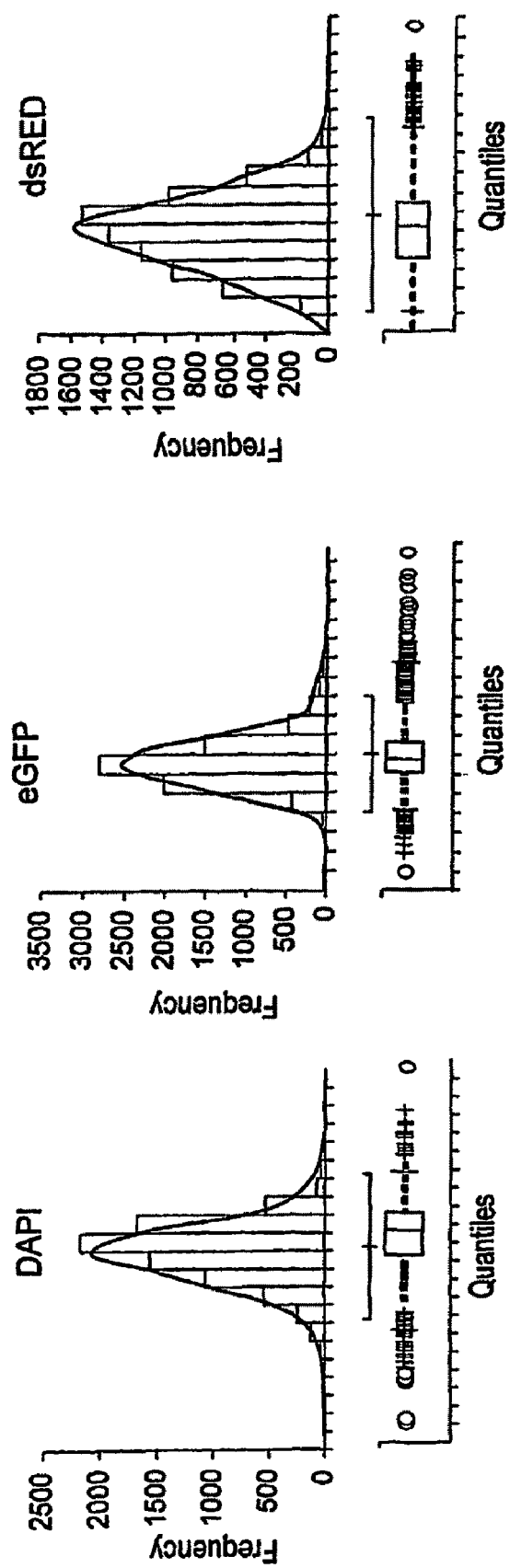
FIG. 3 shows a small-scale screen of 8,000 compounds from the ChemBridge DiverSet library. Summary statistics of the well data in each channel shows normal distributions. X-axis values are quantiles and thus do not reveal that the actual fluorescence intensities of the DAPI distribution were very narrow relative to the distribution of eGFP or dsRED2 intensities, as expected.

Assay Protocol. The following is a detailed assay protocol for the primary assay, i.e., first assay performed in a testing scheme to identify biologically active chemical entities in a screening mode:

Cell Growth, Maintenance and Scale-Up
  Growth at 10% $CO_2$ and 37° C. with approximately 90% relative humidity.
  Growth surface is factory-treated tissue culture plastic.
  Media Formulation: DMEM w/glucose, NaPyruvate, NEAA, pen-strep, 10% Serum.
Cell Seeding
  Cells are seeded ideally at 50-75% confluency in normal growth media.
  Seed time prior to compound addition is 8-24 hr.
Compound Preparation
  Compounds are diluted to 1 mg/mL (~1 mM) in 20% DMSO.
  Compounds are arrayed in given media formulation at approximately 10 μM prior to cell application.
  Compound-arraying is variable and dependent on format of assay. It is desirable to match compound fortified media array format to cell culture plate format.
  Format conversions must be noted and tracking implemented to reconstruct well-compound associations.
Compound Addition to Seeded Cells
  Equivalent volume of 10 uM media is added to untreated media applied at time of cell seeding
  Final nominal compound concentration under cell culture conditions is in an expected μM range.
  Control wells include DMSO vehicle negative controls and positive controls (MG132 for increase; cyclohexamide for negative). In one embodiment each 384-well plate will include 32 control wells divided among negative and positive controls.
Incubation
  Cells are grown for 2 days under described growth conditions without interruption
  Termination—All Reagents and Processes Executed at Room Temperature
  Media is removed from cells and 4% paraformaldehyde is added for a minimum of 40 minutes.
  Paraformaldehyde is washed from wells with at least 1 maximum well volume of PBS.
  Nuclear counterstain is added (DAPI at a concentration of 1 ug/mL) for a minimum of 40 minutes.
  Counterstain is washed from the cells with at least 1 maximum well volume of PBS.
  50% glycerol in ddH2O is added at 0.5× maximum well volume.
Image Collection
  12-bit images collected using 10× objective, 4 fields of view for DAPI, eGFP, and dsRED2 images.
  Flat field correction using calibration images collected and applied to all images.
  In the pilot screen, numerical output data were analyzed in Excel spreadsheets with meta-data providing descriptions of the compound id, dosage, plate and well location and any error flags.
  Normalization of plate to plate variation in image background done using calculated background values and verified by checking distribution of background control wells.
  Object extraction performed by size and intensity thresholding requiring that each object had at least one cell nucleus and this value is presented as an integrated pixel intensity value for each well in DAPI and eGFP color channels (see text).
Data Analysis
  Several criteria could be used to evaluate the image data. For pilot screening, a hit list was compiled from wells that were in bottom and top 0.1 percentiles for eGFP fluorescence AND for which the corresponding dsRED2 and DAPI values were in the central ~10-~90% quantiles. Thumbnail images of these wells were loaded into a spreadsheet, linked to the assay numerical data, and evaluated visually to select hits for further study. The precise quantile cutoffs for the eGFP, dsRED2 and DAPI values were determined empirically based on quantiles in which background wells were excluded but positive control and experimental wells resided. This analysis succeeded in identifying hits that modulated insulin promoter eGFP without causing a severe reduction or increase in cell number and retained dsRED2 (see text). dsRED2 could be analyzed to classify hits further if desired. Visual inspection of thumbnail images is essential to filter out compounds that cause fluorescent crystals or precipitates in the wells.
Equipment/Software for Pilot Screen
  All Systems and Methods are Calibrated and Tested Prior to Screen
  Fluid Handling—Hamilton STAR; Beckman FX/ORCA/SAMI Scheduler
  Plate Indexes—Kendro/Thermo Cytomat6001 and Microplate Hotel
  Imaging—GE/Amersham INCell1000
  Imaging Plate Feeder—Thermo/CRS Catalyst Express Robot Arm
  Image Quantitation—GE/Amersham Developer
  Fluid Handling Tips—MBP/Beckman/Hamilton (10 uL-300 uL)
Microtiter Plates—(Greiner) 96 pp v-bttm; 384 pp v-bttm; 384 Black uClear TC; 1536 Black uClear Lo TC
Results
  Cells plated into 384-well plates were used to screen 8,000 compounds of the ChemBridge DiverSet library were added at one compound per well (5 μM concentration per compound; see protocol). After two days, the plates were fixed in paraformaldehyde and imaged by high-throughput microscopy. The integrated pixel intensity for eGFP, dsRED2 and DAPI fluorescence data per well containing each of the 8,000 screened compounds was measured as in protocol. After normalization across plates, the data points show a normal distribution in all three channels (FIG. 3A-C). As shown in FIG. 3, the actual distribution in the DAPI channel was narrow, reflecting DNA content of cells at various points in the cell cycle. Thus, a preliminary screening of 8,000 compounds from the ChemBridge DiverSet library yielded candidate compounds that regulate the insulin promoter both positively and negatively. A z' value of 0.74 was calculated for the increase in insulin promoter activity and z' value of 0.43 for inhibition of insulin promoter activity.

For a primary confirmatory assay, a dose response curve was performed, with each dose being done with eight replicates over an 20-fold dose range. From the 8,000 compound primary pilot screen, we chose 16 compounds to pursue: 8 with increased and 8 with decreased eGFP fluorescence; all 16 compounds had dsRED2 fluorescence in central quantiles, serving as preliminary filter for compounds that are selective for the insulin promoter. We have confirmed the isolation of compounds that decreased and increased fluorescence in a repeat of the primary screen that tested compounds in replicate and through a dose range. Compounds were observed that increased and decreased eGFP fluorescence. The approximate EC50 values for the compounds in the primary assay were in the low micromolar range.

A z' calculation was performed using one of the positive hits from the primary screen that stimulated an increase in insulin promoter-eGFP response. The z' was calculated to be 0.74 using either media addition alone or DMSO vehicle control wells as the untreated samples. Using the negative control cycloheximide we also calculated a z' for the assay to detect compounds that inhibit insulin promoter activity relative to untreated wells. This z' value for inhibition equaled 0.43. Although less robust than the z' value observed for increased insulin activity, it should be noted that concentrations of cyclohexamide were used that did not cause toxicity during the 48 hr experiment. We expect that selective, non-toxic compounds would produce a better z'.

Compounds that pass the primary confirmatory assay are tested in a secondary confirmatory assay. Secondary assay will be to measure the effect of compounds on endogenous insulin mRNAs by performing, for example, real time polymerase chain reaction (RT-PCR). Both eGFP and endogenous insulin mRNAs will be tested because of the possibility that a compound might affect the 1.4 kb insulin promoter transgene but not the endogenous insulin promoter, which may be under more complex control. Subsequent RNA and protein assays are performed (a) to determine whether compounds affect or modulate genes important for beta-cell or other endocrine cell function, and (b) to identify the signal transduction pathways modulated by the compounds, as described in the section on follow through experiments below.

Additional Embodiments

Once a set of compounds has been identified that includes true positives as defined by the secondary assay, a bioinformatics approach is used to indicate the diversity of signaling affected by the compound set as a whole and to develop hypotheses about the pathways that are modulated by individual molecules. These hypotheses are tested empirically by traditional wet lab approaches. The informatics is performed to aid in identification of intracellular signaling pathways modulated by external stimuli.

We use two information-rich assays that sample the signaling capability and complexity of beta-cells. Changes in mRNA profiles using microarray data are acquired from cells treated with individual compounds over eight time points. Secondly, changes in phosphorylated proteins are acquired by immunoblotting, also over a time course, using phospho-specific antibodies directed towards a panel of intracellular signaling mediators, including Akt, ERK-1 and -2, JNK, MAPK isoforms, PKC isoforms, and Jak-Stat, among others. Gene array and phosphoprotein scan data have been useful to assign signaling pathways and currently comprises the data sets of large-scale signal transduction networking projects (for instance, see http://www.signaling-gateway.org for examples of their application to the definition of signaling networks modulated by extracellular ligands in B-cell and macrophage lines). Recent developments in sophisticated statistical frameworks vastly improve the sensitivity of transcriptome and proteome analyses and consequently enhance their ability to order genes and proteins into signaling pathways. Advanced statistical tools have been applied to identification of genes targeted by thiazolidinedione (TZD) treatment commonly used to increase insulin sensitivity (Hsiao et al., Nucl. Acids Res. 33 (Web Server Issue):W627-632, 2005; Hsiao et al., Bioinformatics 20:3108-3127, 2004), and a phospho-protein scan of RAW 264.7 macrophages treated with a panel of extracellular ligands has been used to predict the pathways that regulate cytokine release (Pradervand et al., Genome Biology 7:R11, 2006).

In addition to collecting and analyzing single ligand gene array and phospho-protein data, pairs of compounds that are found to act through distinct pathways are analyzed here as well. In this way interactions between compounds that combine to give the most robust biological response are examined since these interactions help pinpoint critical nodes in the signaling network.

Experimental Procedures

Transcriptome measurement. Insulinoma cells are treated under optimized conditions with compounds singly and, for a select subset identified as functioning greater than additively, in pairwise manner. Eight time points are obtained in biological triplicates for a total of 24 arrays/compound trial. Consistent with the goal of identifying the immediate response to the compounds, the time points typically span one day (e.g. 0 h, 0.5 h, 1 h, 2 h, 4 h, 8 h, 12 h, 24 h), during which time the immediate signaling response of the compound should have occurred but precede, in at least some cases, overt signs of beta-cell differentiation. Illumina 8.1 BeadArray microarrays are used for these assays.

Phosphoprotein immunoblotting. A panel of antibodies specific for phosphorylated residues in intracellular signaling proteins are tested by ECL (Amersham) immunoblotting on ESCs treated over eight time points. Antibodies (Cell Signal and Sigma) were chosen because their target proteins mediate a broad range of cell signaling. The panel includes phospho-Stat 3 (Tyr705), phospho-Stat6 (Tyr641), phospho-p90RSK (Ser381), phospho-Akt (Ser473), phospho-PKC-pan isoform ($\gamma$ Thr514), phospho-PKC$\delta$ (Tyr311), phospho-PKC$\mu$ (Ser 916), phospho-JNK (Thr183/Tyr185), phosphorylated p44/42 (ERK-1/ERK-2; Thr183, Tyr185 for ERK-2), phospho-p38 MAPK (Thr180/Tyr182), phospho-B-Raf (Ser445), phospho-A-Raf (Ser299), phospho-NF-$\kappa$B (Ser 536), phospho-Smad1/5/8 (Smad1 Ser463/465) and phospho-Smad2 (Ser465/467), phospho-$\beta$-catenin (Thr41/Ser45 and Ser33/37/Thr41) and phospho-GSK3$\beta$ (Ser9). Each of the above are screened for sensitivity and target selectivity against human fetal pancreatic tissue, adult islets, and cell line control samples. Time course for treatment are shorter than for the gene array, and initial studies test 0, 1, 2, 5, 10, 20, 60, and 120 minutes to ensure detection of a response and the time course will be modified as necessary. Potent hits are evaluated singly and pairs that function more than additively (determined in Aim 3) are evaluated in double compound scans.

Transcriptome analysis: Average difference scores for each gene feature are determined using GeneChip Image and Affymetrix MAS 5.0 software. Determination of significant features is done using the VAMPIRE microarray suite (http://genome.ucsd.edu/microarray; Hsiao et al., Nucl. Acids Res. 33 (Web Server Issue):W627-632, 2005; Hsiao et al., Bioinformatics 20:3108-3127, 2004), which achieves high sensitivity from triplicate data sets. Briefly, sensitivity is enhanced by replacing the somewhat arbitrary fold-change cutoff in common use for assessing significant changes in gene expression with a statistically rigorous variance estimate derived from the global set of genes on the chip. Once the gene list is complete, the differentially regulated genes are related to function by annotating all differentially-expressed features with gene names, descriptions, and homologene IDs as well as identifying annotation groups that are statistically enriched among differentially-regulated genes. This is done through the GOby interface of VAMPIRE and reports are automatically generated in Gene Ontology (GO), KEGG, TRANSFAC, Biocarta and Superarray annotation systems.

The Subramaniam laboratory is developing a Biochemical Pathways Workbench which facilitates reconstruction and analysis of signaling pathways. The Workbench will have tools for building pathways from integration of proteomic (in our case phosphoprotein data), and transcriptomic (in conjunction with KEGG, BioCarta and other legacy pathways) and other data derived from literature. Pathways discerned by this analysis will serve as the basis for hypotheses for further experimental design.

Phosphoprotein analysis. Global response patterns of phosphoproteins modulated by single ligands will be visualized using two-way hierarchical clustering of the average levels of the approximately 20 intracellular phosphoproteins at the time point of their maximal (or minimal) response. To further investigate the link between signaling pathway response and beta-cell differentiation, correlation coefficients will be calculated for the association of particular phosphoproteins and the magnitude of the differentiation response, for both the single and double compound treatments. Strong positive and negative correlations will be pursued as they suggest a direct connection between the compound, signaling mediator, and differentiation.

Principal component regression is used to develop models of the signaling relationships between the differentiation response and the phosphoproteins or genes identified in the above analyses. Principal component regression does not require mechanistic knowledge of the proteins, but is an inductive, informatics approach proven to detect underlying patterns and relationships and defines linear models (Janes et al., J. Comput. Biol. 11:544-561, 2004) that will compound to signaling mediators to differentiation. At this point in the analysis, a strong correlation is expected between the principal component regression coefficients and the correlation coefficient for each phosphoprotein that is critically involved in a compound-dependent differentiation pathway.

Model Testing and Interpretation

The pathway models derived from the transcriptome and phosphotome analyses are confirmed by examining interacting the correlating mRNAs and proteins directly in cells stimulated by compound through a dose range. Secondly, other proteins and genes that are known to act in the pathways are evaluated. For instance, if the ERK1/2 proteins are strongly phosphorylated in response to a particular compound, we evaluate MEK proteins as well as potential downstream targets. Iterations of hypothesis devising and testing are used to reveal the signaling pathways and downstream gene targets of active compounds.

Evaluation of genes and phosphoproteins that are stimulated more than additively by pairs of compounds will be quite informative as they are potential nodal points between pathways. It is expected that phosphorylation or gene expression changes of these potential nodal points would correlate with the extent of differentiation. These proteins will be flagged for subsequent studies using gain and loss of function strategies (e.g., overexpression, siRNA, inhibitors, etc.).

Further analysis of the target proteins is accomplished by generating affinity versions of the compounds. Tethering the compound to make an affinity resin is a simple version that has been successful (e.g., Ding et al., Proc. Natl. Acad. Sci. USA 100:7632-7637, 2003). Analogues for covalent labeling of proteins for mass spectroscopy target identification are synthesized for this purpose.

EXAMPLE 2

Screening for Compounds that Modulate Insulin Promoter Activity in TRM-6 Cells

While the promoter elements that determine beta-cell specificity of insulin expression are well understood, the pathways that signal to the insulin promoter have not been investigated extensively, in part because of a lack of in vitro models. That deficiency is particularly acute for human beta-cell models. We have taken advantage of human pancreatic endocrine cell lines that express insulin to assay for small molecules that affect insulin promoter activity. Identifying these compounds and eventually their targets should provide insights into the signaling pathways that control insulin expression.

A primary assay is used to detect compounds that alter expression of an insulin promoter-eGFP reporter cassette in human endocrine cells. A secondary assay of bioactive molecules may be used to verify modulation of the endogenous insulin mRNA by RT-PCR. The primary assay or screen has a z' of >0.6 and has been tested in pilot screens in 384-well plate format. A pilot screen showed that 50% of the most active compounds showed confirmed activity, resulting in molecules that modulate insulin gene activity.

Beta cell models suitable for screens. Beta-cells are the only cell type that express the insulin gene. Therefore, any screen directed at insulin promoter activity is best done using a beta-cell or beta-cell model. Primary beta-cells are in short supply and are difficult to work with, having a strong tendency to undergo apoptosis when manipulated, making them difficult to maintain in monolayer culture, therefore, screens must utilize beta-cell models. Rodent insulinoma cell lines have been studied for many years. In this invention, compounds are screened for effects on insulin promoter activity in the murine beta-cell line Min6. However, there are substantial advantages to be gained by also working with human cells. Human and rodent beta-cells differ in many characteristics, including the number of insulin genes and some features of how the insulin gene is regulated (Odagiri et al., J. Biol. Chem. 271:1909-1915, 1996). Comparing results from two insulin promoter screens, one with human and one with murine cells, assists in mechanistically determining the targets of the compounds and also to prioritize compounds that are studied in greater detail and brought forward into structure-activity and lead optimization studies that involve substantial chemistry resources.

Characteristics of the Human Pancreatic Endocrine Cell Line TRM-6. Cell lines from the human endocrine pancreas have been developed and studied for many years (Follenzi et al., Nature Genet. 25:217-222, 2000; Soneoka et al., Nucl. Acids Res. 23:628-633, 1995; Zufferey et al., Nature Biotechnol. 15:871-875, 1997; Reiser, Gene Ther. 7:910-913, 2000; Ohneda et al., Semin. Cell. Dev. Biol. 11:227-233, 2000; Li et al., J. Biol. Chem. 273:34970-34975, 1998). These human endocrine pancreas cell lines were developed from the human endocrine pancreas using the growth stimulatory genes SV40 T antigen and H-ras$^{val12}$ (Reiser, Gene Ther. 7:910-913, 2000; Ohneda et al., Semin. Cell. Dev. Biol. 11:227-233, 2000; Li et al., J. Biol. Chem. 273:34970-34975, 1998; Hsiao et al., Nucl. Acids Res., 33 (Web Server issue):W627-632, 2005). While the cell lines are immortal and proliferate rapidly in culture, they respond similarly to the great majority of cells that are induced to proliferate by losing differentiated function, particularly hormone gene expression which is why the relationship between growth and differentiation in those cells needs to be understood. In this invention, endocrine differentiation is induced in the cell lines. Some aspects of this invention focus on TRM-6, a cell line derived from human fetal islets, which express insulin in early passages (Follenzi et al., Nature Genet. 25:217-222, 2000; Reiser, Gene Ther. 7:910-913, 2000; Hsiao et al., Bioinformatics 20:3108-3127, 2004). Later passages express substantial levels of somatostatin in response to retroviral vector mediated expression of PDX-1 and aggregate into cell clusters to promote cell-cell contact (Reiser, Gene Ther. 7:910-913, 2000). NeuroD1 repressed somatostatin expression and led to low levels of insulin expression (Follenzi et al., Nature Genet. 25:217-222, 2000).

Figure 4:
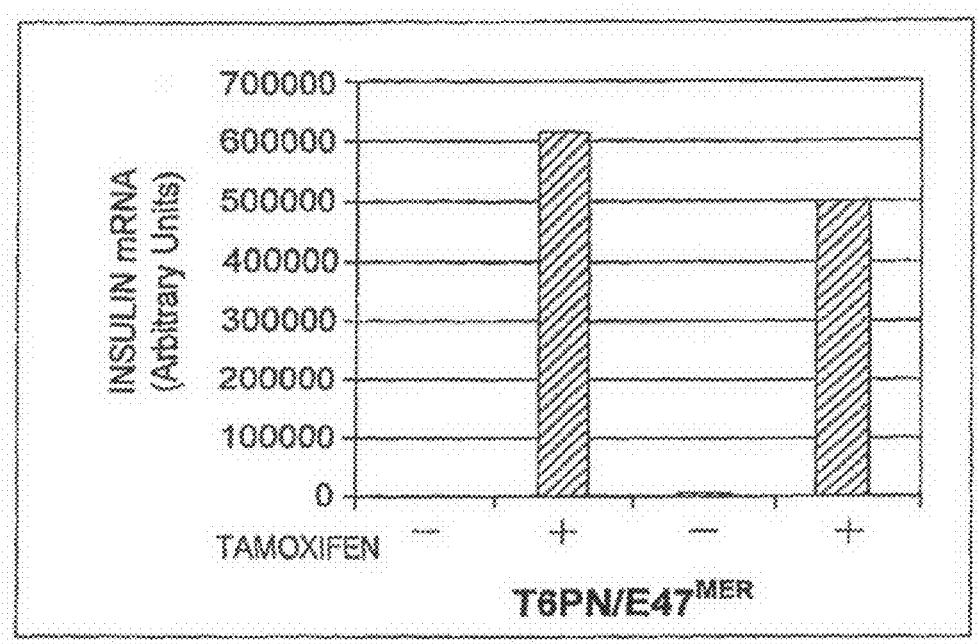
FIG. 4 shows that E47 induces insulin gene expression in T6PN/E47$^{MER}$ cells. (A) Insulin mRNA is barely detectable by non-quantitative RT-PCR in the absence of tamoxifen in two biological replicates of T6PN/E47$^{MER}$ cells. With tamoxifen, insulin mRNA is strongly induced. (B) A different set of two biological replicates of T6PN/E47$^{MER}$ cells were analyzed by quantitative real-time RT-PCR, again demonstrating a dramatic upregulation of insulin mRNA when E47 activity is induced by tamoxifen. The myosin heavy chain gene, which is cardiac specific and highly induced by E-boxes in its promoter, was not induced by tamoxifen (not shown in FIG. 4).

To increase the level of insulin expression, TRM-6 cells expressing PDX-1 and NeuroD1 (T6PN cells) (Follenzi et al., Nature Genet. 25:217-222, 2000) were infected with an E47$^{MER}$ retroviral vector and selected by FACS. E47$^{MER}$ consists of the class I bHLH factor E47 which is a potent insulin transactivator fused to a mutated estrogen receptor that renders it functional only in the presence of tamoxifen. Induction of E47 activity in T6PN cells resulted in induction of much higher levels of insulin gene expression (100-fold) (FIG. 4). To determine whether the effects of E47 were limited to insulin expression or had more general effects on beta-cell differentiation, a panel of other beta-cell genes was examined. E47 was found to induce SUR-1, glucokinase, and MafA. Thus, T6PN/E47$^{MER}$ cells express a substantial number of important beta-cell genes, making them an appropriate target for the insulin promoter screens described herein.

Assay Protocol. The following is a detailed assay protocol for the primary assay, i.e., first assay performed in a testing scheme to identify biologically active chemical entities in a screening mode:

Cell Growth, Maintenance and Scale-Up
   Growth at 10% $CO_2$ and 37° C. with approximately 90% relative humidity
   Growth surface is factory treated tissue culture plastic
   Media formulation DMEM w/glucose, Na Pyruvate, NEAA, pen-strep, 10% Serum
Cell Seeding
   Cells are seeded ideally at 50-75% confluence in media containing 0.5 micromolar tamoxifen
   Seed time prior to compound fortification is 8-24 hr
Compound Preparation
   Compounds are diluted to 1 mg/mL (~1 mM) in 20% DMSO
   Compounds are arrayed in given media formulation at approximately 10 uM prior to cell application
   Compound arraying is variable and dependent on format of assay. It is desirable to match compound fortified media array format to cell culture plate format. In many cases this will involve compound array format conversions which result in operator-defined orientations.
   Format conversions must be noted and tracking implemented to reconstruct well-compound associations
Compound Addition to Seeded Cells
   Equivalent volume of 10 uM media is added to untreated media applied at time of cell seeding
   Final compound concentration under cell culture conditions is ~5 uM
   Control wells include DMSO vehicle negative controls and 4 μM tamoxifen positive control (as in FIG. 2). For pilot screen, each 384-well plate included 32 control wells divided among negative and positive controls.
Incubation
   Cells are grown for 2 days under described growth conditions without interruption
Termination—All Reagents and Processes Executed at Room Temperature
   Media is removed from cells and 4% paraformaldehyde is added for a minimum of 40 minutes
   Paraformaldehyde is washed from wells with at least 1 maximum well volume of PBS
   Nuclear counter-stain is added (most cases DAPI at a concentration of 1 ug/mL) for a minimum of 40 minutes
   Counter-stain is washed from the cells with at least 1 maximum well volume of PBS
   50% glycerol in dd$H_2O$ is added at 0.5 maximum well volume
Image Collection and Analysis
   Images collected using 5× or 10× objective, 1 or 4 fields of view, respectively, for DAPI and eGFP images.
   In the pilot screen, numerical output data were analyzed in Excel spreadsheets with meta-data providing descriptions of the compound id, dosage, plate and well location and any error flags.
   Normalization of plate to plate variation in image background done using calculated background values and verified by checking distribution of background control wells.
   Object extraction performed by size and intensity threshold and this value is presented as an integrated pixel intensity value for each well in DAPI and eGFP color channels (see text).
   Several criteria could be used to evaluate the image data. For pilot screen, thumbnail images from wells from bottom and top 0.1 percentiles in eGFP and DAPI in central 10-90% quantiles were assembled into a spreadsheet, linked to the assay numerical data, and evaluated visually to select hits for further study. This yielded hits that modulated insulin promoter eGFP without causing a severe reduction or increase in cell number (see text).
Equipment/Software for Pilot Screen
   All Systems and Methods are Calibrated and Tested Prior to Screen
   Fluid Handling—Hamilton STAR; Beckman FX/ORCA/SAMI Scheduler
   Plate Indexes—Kendro/Thermo Cytomat6001 and Microplate Hotel
   Imaging—GE/Amersham INCell1000
   Imaging Plate Feeder—Thermo/CRS Catalyst Express Robot Arm
   Image Quantitation—GE/Amersham Developer
   Fluid Handling Tips—MBP/Beckman/Hamilton (10 uL-300 uL)
   Microtiter Plates—(Greiner) 96 pp v-bttm; 384 pp v-bttm; 384 Black uClear TC; 1536 Black uClear Lo TC A human insulin promoter-GFP transgene is faithfully expressed when inserted by lentiviral vector-mediated gene transfer. The lentiviral vector pRRL.SIN-18.cPPT.hINS-EGFP.WPRE that expresses the enhanced green fluorescent protein (EGFP) reporter gene driven by the human insulin gene (hIns) promoter is described in Example 1. RRL.SIN-18.cPPT.hINS-EGFP.WPRE virus was used to infect the mouse insulinoma cell line Min6 and the cervical carcinoma cell line HeLa. High level GFP expression was observed in Min6 but none in HeLa, consistent with the endogenous insulin promoter activity in those cell lines.

eGFP is highly induced in T6PN/E47MER cells by tamoxifen. Once it was clear that the insulin promoter-eGFP lentiviral vector functioned well, T6PN/E47MER cells were infected with it and tested for induction of eGFP by tamoxifen, which induces E47 nuclear translocation and insulin promoter activity. High levels of eGFP were observed in response to tamoxifen administration. This result provided impetus for development of this system into a high-throughput assay.

Figure 5:
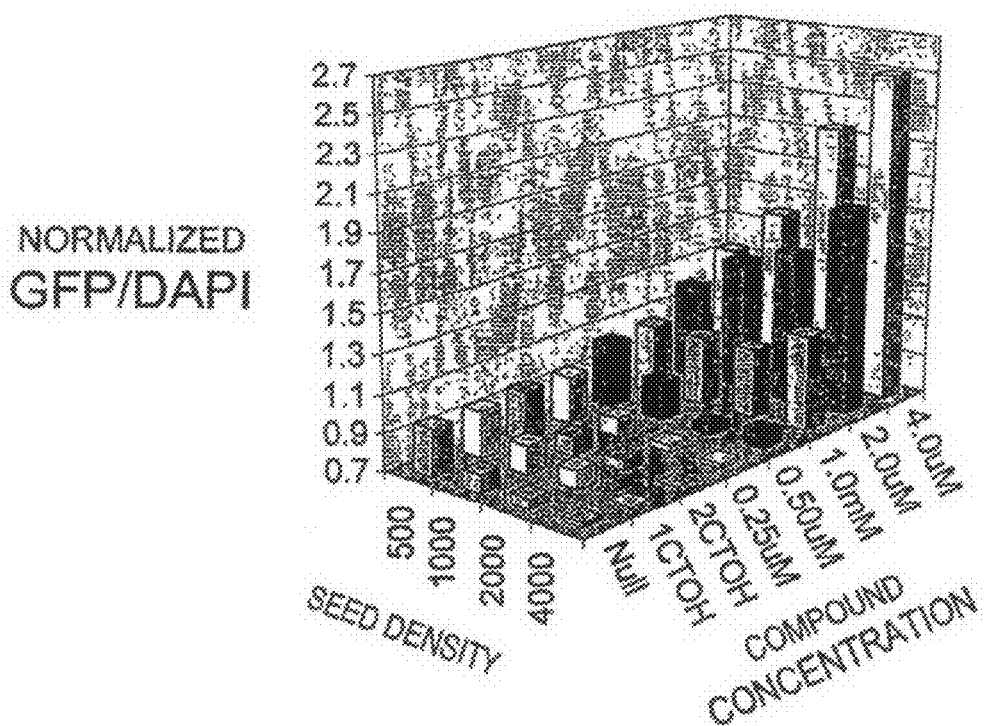
FIG. 5 shows assay optimization to determine seeding density and tamoxifen concentration that result in highest z'. Cells were treated with varying tamoxifen concentrations at different seeding densities and analyzed for the level of eGFP fluorescence normalized to DAPI (to control for cell number).

Optimization of cell plating density and tamoxifen concentration results in a z' values of 0.6. T6PN/E47MER cells infected with the insulin promoter-eGFP virus were tested at different cell plating densities and tamoxifen concentrations and analyzed for the level of eGFP fluorescence normalized to DAPI (to control for cell number) in order to optimize conditions for a high-throughput assay. The results are shown in FIG. 5. Under the optimal conditions in which a baseline of 0.5 micromolar tamoxifen was added to the well and 2,000 cells were plated into each well of a 384 well plate, the calculated z' was 0.6.

Having optimized the assay and validated it with a high z' value, we proceeded with a small-scale screen of a subset of compounds from the ChemBridge DiverSet library.

Preliminary screening of 8,000 compounds from the ChemBridge DiverSet library yields candidate compounds that regulate the insulin promote both positively and negatively. After plating cells into 384 well plates, a submaximal dose of tamoxifen was added to induce an intermediate level of GFP fluorescence and 8,000 compounds of the ChemBridge DiverSet library were added at one compound per well (5 uM concentration per compound; see protocol). After two days, the plates were fixed in paraformaldehyde and the GFP fluorescence was measured by high-throughput microscopy. The integrated eGFP and DAPI fluorescence data per well containing each of the 8,000 screened compounds was measured. To calculate integrated fluorescence intensity, objects were extracted from the images using an intensity- and size-threshold image mask to exclude background and this value was used to select initial hits (see protocol). Four wells illustrating the effect of the small molecule compounds on insulin promoter-GFP fluorescence are shown in FIG. 8. From left to right, there is a control well with no compound demonstrating an intermediate level of GFP fluorescence, a well containing a compound that did not alter insulin promoter activity, a well containing a compound that up-regulated insulin promoter activity, and a well containing a compound that ablated insulin promoter activity. DAPI fluorescence is shown in the corresponding lower panels to demonstrate that the compounds were not toxic to the cells.

Figure 6:
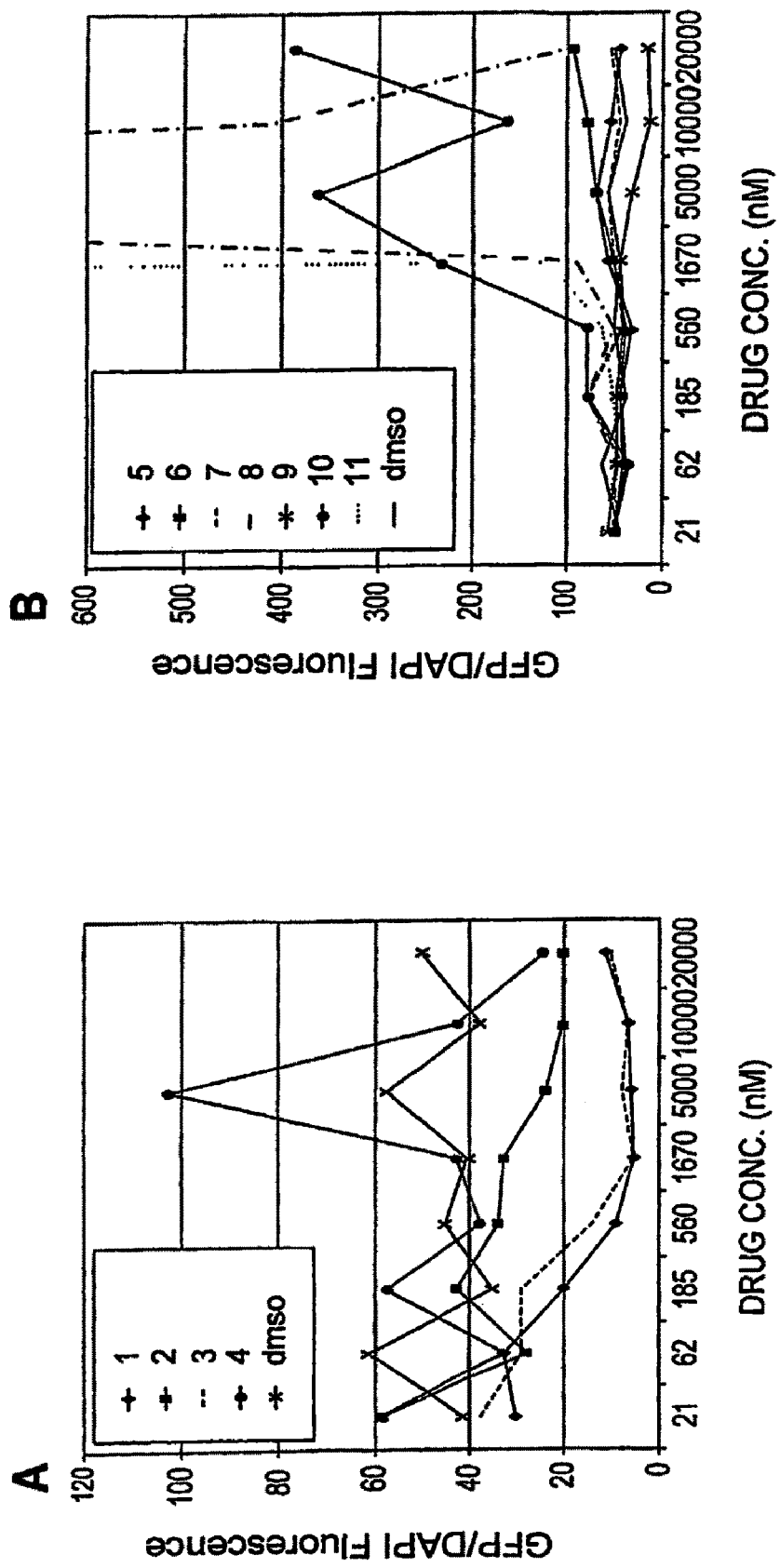
FIG. 6 shows the primary confirmation of selected compounds from the 8,000 compound Chembridge DiverSet library screen. (A) Four compounds randomly selected from 29 compounds that inhibited insulin promoter activity were screened in triplicate at different doses for effects on GFP fluorescence. Two of four compounds were confirmed to inhibit GFP fluorescence. (B) Seven compounds that had the greatest positive effect on GFP fluorescence in the primary screen were tested in triplicate at different doses. Three of the compounds were confirmed to increase GFP fluorescence.

Primary confirmatory assay with dose responsiveness yields a preliminary true positive rate of approximately 50%. For a primary confirmatory assay, a dose response curve was performed, with each dose being done in triplicate (FIG. 6). Three of four compounds that repressed GFP fluorescence and three of seven compounds that increased GFP fluorescence were positive in the confirmatory assay, for a true positive rate of approximately 50% of the initial hits. The approximate EC50 values for the compounds were in the low micromolar range, as expected from the concentration used in the screen (5 micromolar).

Figure 7:
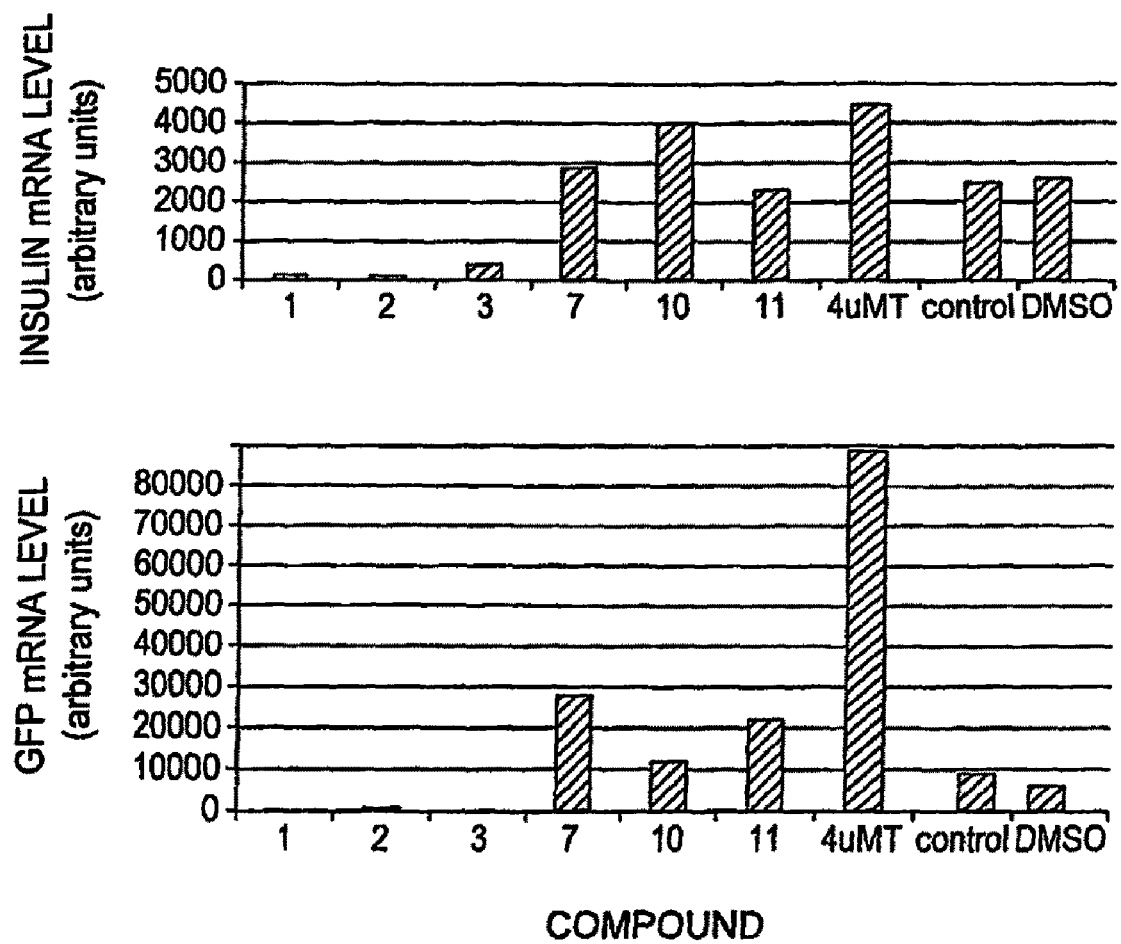
FIG. 7 shows the results of a secondary screen by RT-PCR for insulin and GFP mRNA. Three compounds that repressed GFP fluorescence (1, 2, 3) and three compounds that increased GFP fluorescence (7, 10, 11) were tested for effects on GFP and insulin mRNA. Cells were exposed to 5 micromolar compound and also had 0.5 micromolar tamoxifen. Both controls had 0.5 micromolar tamoxifen and the DMSO control had the same amount of DMSO as was present in the compound-treated samples. The 4 micromolar tamoxifen control represents the maximum induction of insulin mRNA. Both GFP and insulin mRNA levels are normalized for GAPDH mRNA to rule out nonspecific effects of the compounds on transcription.

Second Confirmatory Assay. Compounds that passed the primary confirmatory assay were passed on for further testing in a secondary confirmatory assay. This consisted of RT-PCR of GFP and endogenous insulin mRNA (FIG. 7). Both GFP and endogenous insulin RT-PCR assays are performed because of the possibility that a compound may affect the 1.4 kb insulin promoter transgene but not the endogenous insulin promoter, which may be under more complex control. As shown in FIG. 7, compounds 1, 2, and 3 had potent repressive effects on both GFP and endogenous insulin mRNA. The activating compounds (7, 10, 11) also demonstrated increased insulin mRNA compared to the control containing 0.5 micromolar tamoxifen without any other compound, although compound 10 appears to have the same level of GFP mRNA as control.

Additional Embodiments

Once a set of compounds has been identified that are true positives as defined by the secondary assay, a bioinformatics approach may be used to indicate the diversity of signaling affected by the compound set as a whole and to develop hypotheses about the pathways that are modulated by individual molecules. These hypotheses will be tested empirically by traditional wet lab approaches. The informatics will be performed to aid in the identification of intracellular signaling pathways modulated by external stimuli.

Two information-rich assays that sample the signaling capability and complexity of ESCs are used. Changes in mRNA profiles using microarray data are acquired from cells treated with individual compounds over eight time points. Secondly, changes in phosphorylated proteins are acquired by immunoblotting, also over a time course, using phospho-specific antibodies directed towards a panel of intracellular signaling mediators, including Akt, ERK-1 and -2, JNK, MAPK isoforms, PKC isoforms, and Stat-3, among others. Gene array and phosphoprotein scan data has been useful to assign signaling pathways and currently comprise the data sets of large-scale signal transduction networking projects (for instance, see http://www.signaling-gateway.org for examples of their application to the definition of signaling networks modulated by extracellular ligands in B-cell and macrophage lines). Recent developments in sophisticated statistical frameworks vastly improve the sensitivity of transcriptome and proteome analyses and consequently enhance their ability to order genes and proteins into signaling pathways. Advanced statistical tools developed by Dr. Subramaniam have been applied to identification of genes targeted by thiazolidinedione (TZD) treatment commonly used to increase insulin sensitivity (Hsiao et al., Nucl. Acids Res. 33:W627-6322005; Hsiao et al., Bioinformatics 20:3108-3127, 2004) and to use a phospho-protein scan of RAW 264.7 macrophages treated with a panel of extracellular ligands to predict the pathways that regulate cytokine release (Pradervand et al., Genome Biol. 7:R11, 2006).

In addition to collecting and analyzing single ligand gene array and phospho-protein data, pairs of compounds that are found to act through distinct pathways will be analyzed here as well. The definition of the interactions between compounds that combine to give the most robust biological response is a significant goal since these interactions help pinpoint critical nodes in the signaling network.

Experimental Procedures

Transcriptome Measurement. Insulinoma cells are treated under optimized conditions with compounds singly and, for a select subset identified as functioning greater than additively, in pair-wise manner. Eight time points are obtained in biological triplicates for a total of 24 arrays/compound trial. Consistent with the goal of identifying the immediate response to the compounds, the time points typically span one day (e.g. 0 h, 0.5 h, 1 h, 2 h, 4 h, 8 h, 12 h, 24 h), during which time the immediate signaling response of the compound should have occurred but precede, in at least some cases, overt signs of beta-cell differentiation. Illumina 8.1 BeadArray microarrays are used for these assays.

Phosphoprotein Immunoblotting. A panel of antibodies specific for phosphorylated residues in intracellular signaling proteins are tested by ECL (Amersham) immunoblotting on ESCs treated over eight time points. Antibodies (Cell Signal and Sigma) were chosen because their target proteins mediate a broad range of cell signaling. The panel includes phospho-Stat 3 (Tyr705), phospho-Stat6 (Tyr641), phospho-p90RSK (Ser381), phospho-Akt (Ser473), phospho-PKC-pan isoform (γ Thr514), phospho-PKCδ (Tyr311), phospho-PKC☐ (Ser 916), phospho-JNK (Thr183/Tyr185), phosphorylated p44/42 (ERK-1/ERK-2; Thr183, Tyr185 for ERK-2), phospho-p38 MAPK (Thr180/Tyr182), phospho-B-Raf (Ser445), phospho-A-Raf (Ser299), phospho-NF-κB (Ser 536), phospho-Smad1/5/8 (Smad1 Ser463/465) and phospho-Smad2 (Ser465/467), phospho-β-catenin (Thr41/Ser45 and Ser33/37/Thr41) and phospho-GSK3β (Ser9). Each of the above is screened for sensitivity and target selectivity against human fetal pancreatic tissue, adult islets, and cell line control samples. The time course for treatment is be shorter than for the gene array, and initial studies test 0, 1, 2, 5, 10, 20, 60, and 120 minutes to ensure that detection of a response and the time course will be modified as necessary. Potent hits are evaluated singly and pairs that function more than additively are evaluated in double compound scans.

Transcriptome Analysis. Average difference scores for each gene feature will be determined using GeneChip Image and Affymetrix MAS 5.0 software. Determination of significant features is done using the VAMPIRE microarray suite (http://genome.ucsd.edu/microarray; (Hsiao et al, Nucl. Acids Res. 33:W627-632, 2005; Hsiao et al., Bioinformatics 20:3108-3127, 2004) that achieves high sensitivity from triplicate data sets. Briefly, sensitivity is enhanced by replacing the somewhat arbitrary fold-change cutoff in common use for assessing significant changes in gene expression with a statistically rigorous variance estimate derived from the global set of genes on the chip. Once the gene list is complete, the differentially-regulated genes will be related to function by annotating all differentially-expressed features with gene names, descriptions, and homologene IDs as well as identifying annotation groups that are statistically enriched among differentially-regulated genes. This is done through the GOby interface of VAMPIRE and reports are automatically generated in Gene Ontology (GO), KEGG, TRANSFAC, Biocarta and Superarray annotation systems.

The Subramaniam laboratory is developing a Biochemical Pathways Workbench which facilitates reconstruction and analysis of signaling pathways. The Workbench will have tools for building pathways from integration of proteomic (in our case phosphoprotein data),and transcriptomic (in conjunction with KEGG, BioCarta and other legacy pathways) and other data derived from literature. Pathways discerned by this analysis serve as the basis for hypotheses for further experimental design.

Phosphoprotein analysis: Global response patterns of phosphoproteins modulated by single ligands are visualized using two-way hierarchical clustering of the average levels of the approximately 20 intracellular phosphoproteins at the time point of their maximal (or minimal) response. To further investigate the link between signaling pathway response and beta-cell differentiation, correlation coefficients are calculated for the association of particular phospho-proteins and the magnitude of the differentiation response, for both the single and double compound treatments. Strong positive and negative correlations, are pursued as they suggest a direct connection between the compound, signaling mediator, and differentiation.

Principal component regression are used to develop models of the signaling relationships between the differentiation response and the phosphoproteins or genes identified in the above analyses. Principal component regression does not require mechanistic knowledge of the proteins, but is an inductive, informatics approach proven to detect underlying patterns and relationships and defines linear models (Janes et al., J. Comput. Biol. 11:544-561, 2004) that will link compound to signaling mediators to differentiation. At this point in the analysis, we expect to find a strong correlation between the principal component regression coefficients and the correlation coefficient for each phosphoprotein that is critically involved in a compound-dependent differentiation pathway.

Model Testing and Interpretation. The pathway models derived from the transcriptome and phosphotome analyses are confirmed by interacting the correlating mRNAs and proteins directly in cells stimulated by compound through a dose range. Secondly, other proteins and genes that are known to act in the pathways are evaluated. For instance, if the ERK1/2 proteins are strongly phosphorylated in response to a particular compound, we will evaluate MEK proteins as well as potential downstream targets. Iterations of hypothesis devising and testing reveals the signaling pathways and downstream gene targets of active compounds.

Evaluation of genes and phosphoproteins that are stimulated more than additively by pairs of compounds are quite informative as they are potential nodal points between pathways. It is expected that phosphorylation or gene expression changes of these potential nodal points would correlate with the extent of differentiation. These proteins will be flagged for subsequent studies using gain and loss of function strategies (e.g. over-expression, siRNA, inhibitors).

Further analysis of the target proteins is done by generating affinity versions of the compounds. Tethering the compound to make an affinity resin is a simple version that has been successful (e.g., Ding et al., Proc. Natl. Acad. Sci. USA 100:7632-7637, 2003). Analogues for covalent labeling of proteins for mass spec target identification are being synthesized.

All publications, patents and patent applications are incorporated herein by reference.

While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A human T6PN/E47$^{MER}$ cell comprising a vector, the vector comprising a human insulin gene promoter polynucleotide sequence operably linked to a polynucleotide that encodes a marker polypeptide sequence, wherein the marker polypeptide is expressed upon introduction of the vector into a human T6PN/E47MER cell.

2. The cell of claim 1, wherein the vector is a viral vector.

3. The cell of claim 1, wherein the vector is a lentiviral vector.

4. Lentiviral vector pRRL.SIN-18.cPPT.hINS-EGFP.W-PRE.

5. A cell comprising the vector of claim 4.

6. A pancreatic beta cell comprising the vector of claim 4.

7. A murine cell comprising the vector of claim 4.

8. A MIN6 mouse insulinoma cell comprising the vector of claim 4.

9. A human cell comprising the vector of claim 4.

10. A human T6PN/E47$^{MER}$ cell comprising the vector of claim 4.

11. A human T6PN cell comprising a polynucleotide sequence that expresses E47.

12. The cell of claim 11 comprising a vector that comprises a human insulin gene promoter polynucleotide sequence that is operably linked to a polynucleotide that encodes a marker polypeptide, wherein the marker polypeptide is expressed in the cell.

13. The cell of claim 12 wherein the marker polypeptide is a green fluorescent protein.

14. The cell of claim 12 wherein the marker polypeptide is an enhanced green fluorescent protein.

15. The cell of claim 12 wherein the marker polypeptide is a destabilized green fluorescent protein.

16. The cell of claim 14 wherein the vector is a lentiviral vector.

17. The cell of claim 16 wherein the lentiviral vector is pRRL.SIN-18.cPPT.hINS -EGFP.WPRE.

18. A human T6PN/E47MER cell.

19. The cell of claim 18 comprising a vector that comprises a human insulin gene promoter polynucleotide sequence that is operably linked to a polynucleotide that encodes a marker polypeptide, wherein the marker polypeptide is expressed in the cell.

20. The cell of claim 19 wherein the marker polypeptide is a green fluorescent protein.

21. The cell of claim 19 wherein the marker polypeptide is an enhanced green fluorescent protein.

22. The cell of claim 19 wherein the marker polypeptide is a destabilized green fluorescent protein.

23. The cell of claim 14 wherein the vector is a lentiviral vector.

24. A method of identifying a compound that modulates insulin gene expression, the method comprising: (a) providing a cell comprising a vector that comprises a human insulin gene promoter polynucleotide that is operably linked to a marker polypeptide, wherein the vector is pRRL.SIN-18.cPPT.hINS-EGFP.WPRE, wherein the marker polypeptide is expressed at a baseline level in the cell; (b) contacting the cell with a candidate compound; and (c) detecting a modulation in expression of the marker polypeptide in the cell compared to the baseline level as a result of contacting the cell with the candidate compound.

25. The method of claim 24 comprising determining whether modulation of expression of the marker polypeptide by the candidate compound is dose-responsive.

26. The method of claim 24 comprising determining whether the candidate compound modulates expression of insulin by a mammalian insulin-producing cell.

27. The method of claim 26 comprising determining whether the candidate compound modulates expression of insulin by a mammalian insulin-producing cell by RT-PCR.

28. The method of claim 24 wherein the marker polypeptide is a destabilized green fluorescent protein.

29. The method of claim 24 wherein the cell is a pancreatic beta cell.

30. The method of claim 24 wherein the cell is a murine cell.

31. The method of claim 30 wherein the cell is a MIN6 mouse insulinoma cell.

32. The method of claim 24 wherein the cell is a human cell.

33. The method of claim 32 wherein the cell is a human T6PN/E47$^{MER}$ cell.

34. The method of claim 24 that is automated for high-throughput screening of candidate compounds.

35. A method of identifying a compound that modulates insulin gene expression, the method comprising: (a) providing a cell selected from the group consisting of a MIN6 mouse insulinoma cell and a human T6PN/E47$^{MER}$ cell, the cell comprising a vector that comprises a human insulin gene promoter polynucleotide that is operably linked to an enhanced green fluorescent protein polynucleotide, wherein enhanced green fluorescent protein is expressed at a baseline level in the cell; (b) contacting the cell with a candidate compound; and (c) detecting a modulation in expression of enhanced green fluorescent protein in the cell compared to the baseline level as a result of contacting the cell with the candidate compound.

36. The method of claim 35 wherein the vector is pRRL.SIN-18.cPPT.hINS-EGFP.WPRE.

37. The cell of claim 1 wherein the marker polypeptide is a green fluorescent protein.

38. The cell of claim 1 wherein the marker polypeptide is an enhanced green fluorescent protein.

39. The cell of claim 1 wherein the marker polypeptide is a destabilized green fluorescent protein.

40. The method of claim 24 wherein the marker polypeptide is a green fluorescent protein.

41. The method of claim 24 wherein the marker polypeptide is an enhanced green fluorescent protein.

* * * * *